United States Patent
Barker et al.

(10) Patent No.: US 6,558,912 B1
(45) Date of Patent: May 6, 2003

(54) NRAGE NUCLEIC ACIDS AND POLYPEPTIDES AND USES THEREOF

(75) Inventors: Philip Barker, Westmount (CA); Joseph Verdi, London (CA); Amir Salehi, Point Claire (CA)

(73) Assignees: McGill University, Montreal (CA); Amgen Canada Inc., Mississauge (CA)

( * ) Notice: Subject to any disclaimer, the term of this patent is extended or adjusted under 35 U.S.C. 154(b) by 0 days.

(21) Appl. No.: 09/662,831

(22) Filed: Sep. 15, 2000

Related U.S. Application Data

(60) Provisional application No. 60/154,518, filed on Sep. 16, 1999.

(51) Int. Cl.[7] ............................................. G01N 33/574
(52) U.S. Cl. ........................ 435/7.23; 435/7.1; 435/7.21
(58) Field of Search .............................. 435/4, 7.1, 7.2, 435/7.21, 7.23

(56) References Cited

FOREIGN PATENT DOCUMENTS

| WO | WO 98/29548 | 7/1998 |
|---|---|---|
| WO | WO 99/45944 | 9/1999 |
| WO | WO 00/7528 A2 | 6/2000 |
| WO | WO 00/52022 | 9/2000 |
| WO | WO 00/58473 | 10/2000 |

OTHER PUBLICATIONS

Skolnick et al, TIBTECH vol. 18 p. 34, Jan. 2000.*
Frade, "NRAGE and the cycling side of the neurotrophin receptor p75" Trends in Neurosciences 23:591–592 (2000).
Kendall et al. "Expression analysis of NRAGE: a mage gene signalling an NGF–dependent p75–apoptosis" Society for Neuroscience Abstracts 26: pAbstract No.–3194 (2000).
Miller et al., "Life and death decisions: a biological role for the p75 neurotrophin receptor" Cell Death and DifferentIation 5:343–345 (1998).
Pold et al., "Indentification of a new, unorthodox member of the MAGE gene family" Genomics 59:161–167 (1999).
Salehi et al., "NRAGE, A novel MAGE protein, interacts with the p75 neurotrophin receptor and facilitates nerve growth factor–dependent apoptosis" Neuron 27: 279–288 (2000).

* cited by examiner

*Primary Examiner*—Sheela Huff
(74) *Attorney, Agent, or Firm*—Kristina Bieker-Brady; Clark & Elbing LLP

(57) ABSTRACT

The invention features substantially pure NRAGE polypeptides. The invention also features substantially pure nucleic acids encoding these polypeptides. The polypeptides and nucleic acids of the invention are useful for therapeutic and diagnostic purposes, and for drug discovery.

10 Claims, 4 Drawing Sheets

Human NRAGE
(SEQ ID NO: 1)

MAQKMDCGAGLLGFQAEASVEDSALLMQTLMEAIQISEAPPTNQATAAASPQSSQPPTANEMADIQVSAAAARPKSAF
KVQNATTKGPNGVYDFSQAHNAKDVPNTQPKAAFKSQNATSKGPNAAYDFSQAATTGELAANKSEMAFKAQNATTKVG
PNATYNFSQSLNANDLANSRPKTPFKAWNDTTKAPTADTQTQNVNQAKMATSQADIETDPGISEPDGATAQTSADGSQ
AQNLESRTIIRGKRTRKINNLNVEENSSGDQRRAPLAAGTWRSAPVPVTTQNPPGAPPNVLWQTPLAWQNPSGWQNQT
ARQTPPARQSPPARQTPPAWQNPVAWQNPVIWPNPVIWQNPVIWPNPIVWPGPVVWPNPLAWQNPPGWQTPPGWQTPP
GWQGPPDWQGPPDWPLPPDWPLPPDWPLPTDWPLPPDWIPADWPIPPDWQNLRPSPNLRPSPNSRASQNPGAAQPRDV
ALLQERANKLVKYLMLKDYTKVPIKRSEMLRDIIREYTDVYPEIIERACFVLEKKFGIQLKEIDKEEHLYILISTPES
LAGILGTTKDTPKLGLLLVILGVIFMNGNRASEAVLWEALRKMGLRPGVRHPLLGDLRKLLTYEFVKQKYLDYRRVPN
SNPPEYEFLWGLRSYHETSKMKVLRFIAEVQKRDPRDWTAQFMEAADEALDALDAAAAEAEARAEARTRMGIGDEAVS
GPWSWDDIEFELLTWDEEGDFGDPWSRIPFTFWARYHQNARSRFPQTFAGPIIGPGGTASANFAANFGAIGFFWVE

Fig. 1A

Rat NRAGE
(SEQ ID NO: 2)

MAQKPDGGAGLRGFQAEASVEDSALLVQTLMEAIQISEAPPTSQATAAASGPNASPQSSQPPTANEKADTEVSAAAAR
PKTGFKAQNTTTKGPNDYSQARNAKEMPKNQPKVAFKSQNATSKGPHAASDFSHAASTGKSAAKKSEMAFKGQNTTTK
AGPSATYNFTQSPSANEMTNNQPKTAKAWNDTTKIPGADAQTQNVNQAKMADVGTSAGISETDGAAAQTSADGSQAQN
VESRTIIRGKRTRKINNLNVEENSNGDQRRASLASGNWRSAPVPVTTQNPPGAPPNVLWQTPLAWQNPSGWQNQTARQ
TPPARQSPPARQTPSAWQNPVAWQNPVIWPNPVIWQNPVIWPNPIVWPGPIVWPNPMAWQSTPGWQSPPSWQAPPSWQ
SPQDWQGPPDWQLPPDWSMPPDWSFPSDWPFPPDWIPADWPIPPDWQNLRPSPNLRSSPNSRASQNQGPPQPRDVALL
QERANKLVKYLMLKDYTKVPIKRSEMLRDIIREYTDVYPEIIERACFVLEKKFGIQLKEIDKEEHLYILISTPESLAG
ILGTTKDTPKLGLLLVILGIIFMNGNRATEAVLWEALRKMGLRPGVRHPLLGDLRKLLTYEFVKQKYLDYRRVPNSNP
PEYEFLWGLRSYHETSKMKVLRFIAEVQKRDPRDWTAQFMEAADEALDALDAAAAEAEARAEARNRMGIGDEAVSGPW
SWDDIEFELLTWDEEGDFGDPWSRIPFTFWARYHQNARSRFPQAFTGPIIGPSGTATANFAANFGAIGFFWVE

Fig. 1B

Human NRAGE
SEQ ID NO: 3

```
GGCACGAGGAGAGTGCGGCTGCTGAGAGCCGAGCCCAGCAATCCCGATCCTCTGAGTCGTGAAGAAGGGA
GGCAGCGAGGGGGTTGGGGTTGGGGCCTGAGAAGCCCCCAGGCTCCGCTCTTGCCAGAGGGACAGGAGCC
ATGGCCCAGAAAATGGACTGTGGTGCGGGCCTCCTCGGCTTCCAGGCTGAGGCCTCCGTAGAAGACAGCG
CCTTGCTTATGCAGACCTTGATGGAGGCCATCCAGATCTCAGAGGCTCCACCTACTAACCAGGCCACCGC
AGCTGCTAGTCCCCAGAGTTCACAGCCCCCAACTGCCAATGAGATGGCTGACATTCAGGTTTCAGCAGCT
GCCGCTAGGCCTAAGTCAGCCTTTAAAGTCCAGAATGCCACCACAAAAGGCCCAAATGGTGTCTATGATT
TCTCTCAGGCTCATAATGCCAAGGATGTGCCCAACACGCAGCCCAAGGCAGCCTTTAAGTCCCAAAATGC
TACCTCCAAAGGTCCAAATGCTGCCTATGATTTTTCCCAGGCAGCAACCACTGGTGAGTTAGCTGCTAAC
AAGTCTGAGATGGCCTTCAAGGCCCAGAATGCCACTACTAAAGTGGGCCCAAATGCCACCTACAATTTCT
CTCAGTCTCTCAATGCCAATGACCTGGCCAACAGCAGGCCTAAGACCCCTTTCAAGGCTTGGAATGATAC
CACTAAGGCCCCAACAGCTGATACCCAGACCCAGAATGTAAATCAGGCCAAAATGGCCACTTCCCAGGCT
GACATAGAGACCGACCCAGGTATCTCTGAACCTGACGGTGCAACTGCACAGACATCAGCAGATGGTTCCC
AGGCTCAGAATCTGGAGTCCCGGACAATAATTCGGGGCAAGAGGACCCGCAAGATTAATAACTTGAATGT
TGAAGAGAACAGCAGTGGGGATCAGAGGCGGGCCCCACTGGCTGCAGGGACCTGGAGGTCTGCACCAGTT
CCAGTGACCACTCAGAACCCACCTGGCGCACCCCCCAATGTGCTCTGGCAGACGCCATTGGCTTGGCAGA
ACCCCTCAGGCTGGCAAAACCAGACAGCCAGGCAGACCCCACCAGCACGTCAGAGCCCTCCAGCTAGGCA
GACCCCACCAGCCTGGCAGAACCCAGTCGCTTGGCAGAACCCAGTGATTTGGCCAAACCCAGTAATCTGG
CAGAACCCAGTGATCTGGCCAAACCCCATTGTCTGGCCCGGCCCTGTTGTCTGGCCGAATCCACTGGCCT
GGCAGAATCCACCTGGATGGCAGACTCCACCTGGATGGCAGACCCCACCGGGCTGGCAGGGTCCTCCAGA
CTGGCAAGGTCCTCCTGACTGGCCGCTACCACCCGACTGGCCACTGCCACCTGATTGGCCACTTCCCACT
GACTGGCCACTACCACCTGACTGGATCCCCGCTGATTGGCCAATTCCACCTGACTGGCAGAACCTGCGCC
CCTCGCCTAACCTGCGCCCTTCTCCCAACTCGCGTGCCTCACAGAACCCAGGTGCTGCACAGCCCCGAGA
TGTGGCCCTTCTTCAGGAAAGAGCAAATAAGTTGGTCAAGTACTTGATGCTTAAGGACTACACAAAGGTG
CCCATCAAGCGCTCAGAAATGCTGAGAGATATCATCCGTGAATACACTGATGTTTATCCAGAAATCATTG
AACGTGCATGCTTTGTCCTAGAGAAGAAATTTGGGATTCAACTGAAAGAAATTGACAAAGAAGAACACCT
GTATATTCTCATCAGTACCCCCGAGTCCCTGGCTGGCATACTGGGAACGACCAAAGACACACCCAAGCTC
GGTCTCCTCTTGGTGATTCTGGGTGTCATCTTCATGAATGGCAACCGTGCCAGTGAGGCTGTCCTCTGGG
AGGCACTACGCAAGATGGGACTGCGTCCTGGGGTGAGACATCCCCTCCTTGGAGATCTAAGGAAACTTCT
CACCTATGAGTTTGTAAAGCAGAAATACCTGGACTACAGACGAGTGCCCAACAGCAACCCCCCGGAGTAT
GAGTTCCTCTGGGGCCTCCGTTCCTACCATGAGACTAGCAAGATGAAAGTGCTGAGATTCATTGCAGAGG
TTCAGAzAAGAGACCCTCGTGACTGGACTGCACAGTTCATGGAGGCTGCAGATGAGGCCTTGGATGCTCT
GGATGCTGCTGCAGCTGAGGCCGAAGCCCGGGCTGAAGCAAGAACCCGCATGGGAATTGGAGATGAGGCT
GTGTCTGGGCCCTGGAGCTGGGATGACATTGAGTTTGAGCTGCTGACCTGGGATGAGGAAGGAGATTTTG
GAGATCCCTGGTCCAGAATTCCATTTACCTTCTGGGCCAGATACCACCAGAATGCCCGCTCCAGATTCCC
TCAGACCTTTGCCGGTCCCATTATTGGTCCTGGTGGTACAGCCAGTGCCAACTTCGCTGCCAACTTTGGT
GCCATTGGTTTCTTCTGGGTTGAGTGAGATGTTGGATATTGCTATCAATCGCAGTAGTCTTTCCCCTGTG
TGAGCTGAAGCCTCAGATTCCTTCTAAACACAGCTATCTAGAGAGCCACATCCTGTTGACTGAAAGTGGC
ATGCAAGATAAATTTATTTGCTGTTCCTTGTCTACTGCTTTTTTTCCCCTTGTGTGCTGTCAAGTTTTGG
TATCAGAAATAAACATTGAAATTGCAAAGTGAAAAAAAAAAAAAAAAAAAAA
```

Fig. 1C

Rat NRAGE
SEQ ID NO: 4

```
CGGCCGCGTCGACCGGGACTCTTATTTGGACAGTGATCTGTTGCGCATGCGCGGGGCTTCCTGAGGCGGT
GGGTGGTATATTAGGCGAAGAGGCGGGGTCGCCCGAGCTGCCGCGCTGGCATTTTCTCCTGGACAAGGAG
AGAGTGCGGGTGCAGAGAGCGGAGCAGAGCAGTCCCGATCCTCTGAGTCGTGAAGAAGGAAGCAACGAAG
GGGGTTGGGGTTGGGGCCTGAGGCAAGGCTCTGCTCTTGCCAGAGAGACAAGAGCTATGGCTCAGAAACC
GGACGGCGGTGCAGGCCTCCGCGGCTTCCAGGCAGAGGCCTCTGTAGAAGACAGCGCCTTGCTTGTGCAG
ACCTTGATGGAAGCCATCCAGATCTCCGAGGCTCCGCCCACCAGCCAGGCCACAGCAGCTGCCAGTGGGC
CGAATGCTAGTCCCCAGAGTTCACAGCCCCCAACTGCCAATGAGAAGGCTGATACTGAGGTTTCAGCAGC
TGCTGCCAGGCCTAAGACAGGCTTTAAGGCCCAGAATACCACCACAAAGGGGCCAAATGATTACTCTCAG
GCACGTAATGCCAAGGAGATGCCCAAGAATCAGCCTAAGGTGGCCTTTAAGTCACAGAATGCCACCTCTA
AAGGTCCACATGCTGCCTCTGATTTTTCCCATGCAGCATCCACAGGCAAATCAGCAGCTAAAAAGTCTGA
AATGGCCTTTAAGGGTCAGAATACCACTACTAAGGCTGGCCCCAGTGCCACCTACAATTTCACTCAGTCT
CCCAGTGCCAATGAGATGACCAACAACCAGCCTAAGACAGCTAAGGCTTGGAATGACACCACTAAGATCC
CTGGAGCTGATGCCCAGACCCAGAATGTAAACCAGGCCAAAATGGCTGACGTAGGGACCAGTGCAGGTAT
CTCTGAAACTGACGGTGCAGCAGCCCAGACCTCAGCAGATGGCTCCCAGGCTCAGAATGTGGAGTCCCGG
ACTATAATTCGGGGCAAGAGGACCCGCAAGATTAATAACTTGAATGTGGAAGAGAACAGCAATGGGGACC
AAAGGCGTGCCTCGCTGGCTTCCGGGAACTGGAGGTCTGCTCCGGTTCCAGTAACCACTCAGAACCCACC
TGGCGCACCCCCTAATGTGCTGTGGCAGACACCACTGGCTTGGCAGAACCCATCAGGCTGGCAAAACCAG
ACAGCCAGGCAGACCCCACCAGCACGTCAGAGTCCCCAGCTAGGCAGACACCATCAGCTTGGCAGAACC
CCGTTGCATGGCAGAATCCAGTGATCTGGCCTAACCCAGTGATCTGGCAGAATCCAGTGATCTGGCCAAA
CCCCATTGTCTGGCCTGGCCCAATTGTCTGGCCAAACCCAATGGCCTGGCAGAGTACACCTGGATGGCAG
AGCCCACCCAGTTGGCAGGCTCCACCTAGTTGGCAGAGCCCTCAAGATTGGCAAGGCCCTCCAGATTGGC
AGTTACCACCTGACTGGTCAATGCCTCCTGACTGGTCCTTTCCCTCTGACTGGCCTTTTCCACCTGACTG
GATCCCTGCCGACTGGCCAATTCCACCCGACTGGCAGAACTTACGACCCTCACCTAATCTGAGATCCTCC
CCCAACTCTCGTGCCTCACAGAACCAGGGTCCTCCACAGCCCCGAGATGTGGCCCTTCTTCAGGAAAGAG
CAAATAAGCTGGTCAAGTACTTGATGCTTAAAGACTACACGAAGGTGCCCATCAAGCGCTCAGAAATGCT
GAGAGATATCATCCGAGAATACACTGATGTTTATCCAGAAATCATTGAACGCGCATGCTTTGTCCTGGAG
AAGAAATTTGGAATCCAGCTCAAGGAAATCGACAAAGAAGAGCATCTGTATATCCTCATCAGTACCCCTG
AATCCCTGGCTGGCATACTGGGAACGACCAAAGACACACCGAAGCTAGGCCTCCTCTTAGTGATTCTGGG
CATTATCTTCATGAATGGCAACCGTGCCACTGAGGCCGTCCTCTGGGAAGCACTGCGCAAGATGGGACTA
CGTCCTGGGGTCAGACATCCCCTCCTTGGCGATCTGAGGAAACTTCTTACTTACGAGTTTGTAAAGCAGA
AATACCTGGACTACAGACGAGTGCCCAACAGCAACCCTCCTGAGTATGAGTTCCTCTGGGCCTCCGCTC
CTACCATGAGACTAGCAAGATGAAAGTGCTGAGATTCATTGCAGAGGTTCAGAAGAGAGACCCTCGTGAC
TGGACTGCACAGTTCATGGAAGCTGCAGATGAAGCCTTGGATGCTCTGGATGCTGCTGCAGCTGAGGCAG
AGGCCCGGGCCGAAGCAAGAAACCGCATGGGATTGGAGACGAGGCTGTGTCTGGGCCCTGGAGCTGGGA
TGACATTGAGTTTGAGCTGCTGACCTGGGATGAGGAAGGAGATTTTGGAGATCCTTGGTCCAGGATCCCC
TTTACCTTCTGGGCCAGATACCACCAGAATGCCCGCTCCAGGTTTCCCCAGGCCTTTACCGGCCCCATCA
TTGGCCCCAGCGGCACTGCCACCGCCAACTTCGCCGCCAACTTCGGTGCCATTGGCTTCTTCTGGGTTGA
GTAAAGTGTCAGATACTGCTCATCATTTGCAATAGTTTTCCCTGAGTGAGGCTGAAGCCTCAGATTCCTT
CAAAACACAGCTATCTAGAGAGCCACATCCTGTTGACTGAGAGTGGCATGCAAGATAAATTTATTTGCTA
TTCTGTCTATTACTTTTTTTTCCTTGTCTGTTGTCAAGTTTTGGTATCAGAAATAAATGTTGAAATTGCA
AAGTGAAAAAAAAAAAAAAAAAA
```

NRAGE NUCLEIC ACIDS AND POLYPEPTIDES AND USES THEREOF

CROSS-REFERENCE TO RELATED APPLICATIONS

This application claims benefit of U.S. Provisional Application Serial No. 60/154,518, filed Sep. 16, 1999 (now pending), hereby incorporated by reference.

BACKGROUND OF THE INVENTION

The invention relates to proteins involved in neurotrophin signaling.

The regulation of cell growth and survival is believed to be under the control of a wide variety of signaling cascades. One such cascade is that which transduces the presence of a neurotrophin ligand. Early in vivo and in vitro experiments demonstrated that nerve growth factor (NGF) plays critical roles in the development of the nervous system. The cloning of brain-derived neurotrophic factor (BDNF) subsequently revealed a homology with NGF that spurred the cloning and characterization of neurotrophin-3 (NT-3), neurotrophin-4/5 (NT-4/5) and neurotrophin-6 (NT-6). Each of these proteins promotes survival of specific populations of neurons and affects aspects of the neuronal phenotype.

The mammalian neurotrophins interact with two types of cell surface receptors. The trk receptors (e.g., trkA, trkB, and trkC) are highly-related transmembrane receptor tyrosine kinases, each of which preferentially binds one or a subset of the neurotrophin family members trk receptors play a critical role in mediating the effects of the neurotrophins, and their activation results in the effects typically associated with neurotrophin action.

The p75NTR receptor (p75NTR), which binds all neurotrophins with approximately equal affinity, is a member of the tumor necrosis factor (TNF) receptor superfamily. In contrast to the rapid progress made in elucidating the mechanism of action of the trk receptors, the physiological roles of the p75NTR have been more difficult to discern. At present, the actions of p75NTR fall into two categories. First, p75NTR appears to functionally collaborate with trk receptors to either enhance or reduce neurotrophin-mediated trk receptor activation. Second, p75NTR acts autonomously to activate signaling cascades that may be involved in apoptosis and inflammation.

A number of proteins which directly interact with the intracellular domains of members of the TNF receptor superfamily have been identified, including TRADD, FADD, and members of the TRAF family. Generally, the intracellular domain of p75NTR is highly conserved across species, but not conserved with other members of the TNF receptor superfamily. The exception to the general lack of homology between p75NTR and the TNF receptor superfamily is the presence of a 90 amino acid stretch termed the "death domain." In TNF receptor-1 (TNFR-1), fas, DR3, and other related receptors, the death domain is required to mediate interactions with either FADD or TRADD. We have previously found, however, that the p75NTR does not bind TRADD or FADD proteins. The failure of p75NTR to bind FADD or TRADD is likely due to the fact that the tertiary structure of the p75NTR death domain differs considerably from these other, receptors, suggesting that p75NTR must facilitate apoptosis through another mechanism. Thus, the mechanism by which neurotrophins signal via p75NTR to modulate apoptosis remains unknown.

There is a need to identify additional components of the neurotrophin signal transduction pathway. These components would be useful as targets for pharmacologic intervention in patients diagnosed with an apoptotic disease.

SUMMARY OF THE INVENTION

In a first aspect, the invention features a substantially pure NRAGE polypeptide (previously referred to as PRIMAGE). In a preferred embodiment, the polypeptide is from a mammal (e.g., a human). In a second preferred embodiment, the polypeptide binds to p75NTR.

In a second aspect, the invention features a substantially pure polypeptide having 50% or greater amino acid sequence identity to the amino acid sequence of the protein of the first aspect and binds to p75NTR. Preferably, the polypeptide has 70% or greater amino acid sequence identity to the amino acid sequence of the protein of the first aspect and binds to p75NTR. More preferably, the polypeptide has 85% or greater amino acid sequence identity to the amino acid sequence of the protein of the first aspect and binds to p75NTR.

In a third aspect, the invention features a substantially pure polypeptide that modulates apoptosis, wherein the polypeptide has 50% or greater amino acid sequence identity to an amino acid sequence of SEQ ID NO: 1 or SEQ ID NO: 2.

Preferably, the polypeptide has 70% or greater amino acid sequence identity to the amino acid sequence of SEQ ID NO: 1 or SEQ ID NO: 2. More preferably, the polypeptide has 80% or greater amino acid sequence identity to the amino acid sequence of SEQ ID NO: 1 or SEQ ID NO: 2.

In a fourth aspect, the invention features a substantially pure nucleic acid molecule encoding an NRAGE polypeptide. In one embodiment, the nucleic acid molecule is from a mammal (e.g., a human). In another embodiment, the nucleic acid is cDNA.

In a fifth aspect, the invention features substantially pure DNA having a sequence of FIG. 1C (SEQ ID NO: 3) or FIG. 1D (SEQ ID NO: 4), or degenerate variants thereof, and encoding an amino, acid sequence of FIG. 1A (SEQ ID NO: 1) or FIG. 1B (SEQ ID NO: 2).

In a sixth aspect, the invention features substantially pure DNA that binds at high stringency to a DNA sequence of FIG. 1C (SEQ ID NO: 3) or FIG. 1D (SEQ ID NO: 4).

In a seventh aspect, the invention features purified DNA sequence substantially identical to a DNA sequence shown in FIG. 1C (SEQ ID NO: 3) or FIG. 1D (SEQ ID NO: 4).

In one embodiment, the nucleic acid is operably linked to regulatory sequences for expression of the polypeptide encoded by the nucleic acid and wherein the regulatory sequences comprise a promoter. Preferably, the promoter is a constitutive promoter, is inducible by one or more external agents, or is cell-type specific.

In an eighth aspect, the invention features a vector that includes the nucleic acid of the seventh aspect, the vector being capable of directing expression of the polypeptide encoded by the nucleic acid in a vector-containing cell.

In a ninth aspect, the invention features a cell expressing the nucleic acid of the seventh aspect.

In a tenth aspect, the invention features a method for identifying a compound that modulates binding of NRAGE to p75NTR. The method includes: (a) providing a cell expressing an NRAGE polypeptide; (b) contacting the cell with a candidate compound; and (c) monitoring the level of binding of the NRAGE polypeptide to p75NTR, wherein a change in the level of the binding in response to the candidate compound relative to a level of binding in a cell not contacted with the candidate compound indicating the presence of a compound that modulates binding of NRAGE to p75NTR. Preferably, the cell is from a mammal (e.g., a human or a rodent).

In an eleventh aspect, the invention features a kit for determining the amount of NRAGE polypeptide in a sample, the kit including a substantially pure antibody that specifically binds an NRAGE polypeptide. Preferably, the kit further includes a means for detecting the binding of the antibody to the NRAGE polypeptide.

In a twelfth aspect, the invention feature a substantially pure antibody that specifically binds to an NRAGE polypeptide. In one embodiment, the antibody is selected from a group consisting of a polyclonal antibody, a monoclonal antibody, and a neutralizing antibody.

In a thirteenth aspect, the invention features a method for modulating cell apoptosis, the method includes administering an NRAGE polypeptide to the cell.

In a fourteenth aspect, the invention features a method for modulating apoptosis. The method includes administering to the cell a compound that modulates binding of NRAGE to p75NTR. In various embodiments, the compound is a chemical, a drug, or an antibody that specifically binds to an NRAGE polypeptide. A preferred antibody is a neutralizing antibody. In one preferred embodiment, the compound is an NRAGE antisense nucleic acid molecule.

In preferred embodiments of the thirteenth or fourteenth aspect, the cell is in a mammal (e.g., a human or a rodent).

In another embodiment of the thirteenth or fourteenth aspects, apoptosis is decreased in a mammal diagnosed as being HIV-positive, or as having AIDS, cirrhosis of the liver, a neurodegenerative disease, a myelodysplastic syndrome, or an ischemic injury.

In yet another embodiment of the thirteenth or fourteenth aspects, apoptosis is increased in a mammal diagnosed as having a cell proliferation disease.

In a fifteenth aspect, the invention features a therapeutic composition having as an active ingredient an NRAGE polypeptide, an antibody that specifically binds an NRAGE polypeptide, or an NRAGE antisense nucleic acid molecule, the active ingredient being formulated in a physiologically acceptable carrier. Preferably, the composition modulates cell apoptosis.

In a sixteenth aspect, the invention features a method for identifying a compound that modulates p75NTR biological activity. The method includes (a) providing a cell expressing an NRAGE polypeptide; (b) exposing the cell to a candidate compound; and (c) monitoring the level of expression of the NRAGE polypeptide, a change in the level of expression in response to the candidate compound relative to a level of expression in a cell not contacted with the candidate compound indicating the presence of a compound that modulates p75NTR biological activity.

In a seventeenth aspect, the invention features a method for identifying a compound that modulates p75NTR biological activity. The method includes (a) providing a cell expressing an NRAGE polypeptide capable of binding to p75NTR; (b) contacting the cell with a candidate compound; and (c) monitoring the level of the binding of the NRAGE polypeptide to p75NTR, a change in the level of binding in response to the candidate compound relative to a level of binding in a cell not contacted with the candidate compound indicating the presence of a compound that modulates p75NTR biological activity.

In a preferred embodiment of the sixteenth or seventeenth aspect, the cell is from a mammal (e.g., a human or a rodent).

By "polypeptide" is meant any chain of more than two amino acids, regardless of post-translational modification, such as glycosylation or phosphorylation.

NRAGE polypeptides that are a part of the invention include those polypeptides that bind to p75NTR, are capable of binding an antibody which specifically binds NRAGE, or modulate p75NTR biological activity in a cell. Preferred NRAGE polypeptides are those represented by the amino acid sequences of SEQ ID NO: 1 (FIG. 1A) and SEQ ID NO: 2 (FIG. 1B).

NRAGE nucleic acids that are a part of the invention include those nucleic acids encoding polypeptides that bind to p75NTR, are capable of binding an antibody which specifically binds NRAGE, or modulate p75NTR biological activity in a cell. Preferred NRAGE nucleic acids are those represented by the nucleotide sequences of SEQ ID NO: 3 (FIG. 1C) and SEQ ID NO: 4 (FIG. 1D).

By "substantially identical" is meant a polypeptide or nucleic acid exhibiting at least 50%, preferably 85%, more preferably 90%, and most preferably 95% identity to a reference amino acid or nucleic acid sequence. For polypeptides, the length of comparison sequences will generally be at least 16 amino acids, preferably at least 20 amino acids, more preferably at least 25 amino acids, and most preferably 35 amino acids. For nucleic acids, the length of comparison sequences will generally be at least 50 nucleotides, preferably at least 60 nucleotides, more preferably at least 75 nucleotides, and most preferably 110 nucleotides.

Sequence identity is typically measured using sequence analysis software with the default parameters specified therein (e.g., Sequence Analysis Software Package of the Genetics Computer Group, University of Wisconsin Biotechnology Center, 1710 University Avenue, Madison, Wis. 53705). This software program matches similar sequences by assigning degrees of homology to various substitutions, deletions, and other modifications. Conservative substitutions typically include substitutions within the following groups: glycine, alanine, valine, isoleucine, leucine; aspartic acid, glutamic acid, asparagine, glutamine; serine, threonine; lysine, arginine; and phenylalanine, tyrosine.

By "high stringency conditions" is meant hybridization in 2×SSC at 40° C. with a DNA probe length of at least 40 nucleotides. For other definitions of high stringency conditions, see F. Ausubel et al., *Current Protocols in Molecular Biology*, pp. 6.3.1–6.3.6, John Wiley & Sons, New York, N.Y., 1994, hereby incorporated by reference.

By "p75NTR biological activity" is meant binding to NRAGE, modulating p75NTR-mediated apoptosis, or any other p75NTR-mediated activity known in the art. Additional examples are provided, for example, in Barker (Cell Death Differ. 5:346–356, 1998) and Miller and Kaplan (Cell Death Differ. 5:343–345, 1998).

By "substantially pure polypeptide" is meant a polypeptide that has been separated from the components that naturally accompany it. Typically, the polypeptide is substantially pure when it is at least 60%, by weight, free from the proteins and naturally-occurring organic molecules with which it is naturally associated. Preferably, the polypeptide is an NRAGE polypeptide that is at least 75%, more preferably at least 90%, and most preferably at least 99%, by weight, pure. A substantially pure NRAGE polypeptide may be obtained, for example, by extraction from a natural source (e.g., a neuronal cell), by expression of a recombinant nucleic acid encoding an NRAGE polypeptide, or by chemically synthesizing the protein. Purity can be measured by any appropriate method, e.g., by column chromatography, polyacrylamide gel electrophoresis, or HPLC analysis.

A polypeptide is substantially free of naturally associated components when it is separated from those contaminants that accompany it in its natural state. Thus, a polypeptide which is chemically synthesized or produced in a cellular system different from the cell from which it naturally originates will be substantially free from its naturally associated components. Accordingly, substantially pure polypeptides include those which naturally occur in eukaryotic organisms but are synthesized in E. coli or other prokaryotes.

By "substantially pure nucleic acid" is meant nucleic acid that is free of the genes which, in the naturally-occurring genome of the organism from which the nucleic acid of the invention is derived, flank the nucleic acid. The term therefore includes, for example, a recombinant nucleic acid that is incorporated into a vector; into an autonomously replicating plasmid or virus; into the genomic nucleic acid of a prokaryote or a eukaryote cell; or that exists as a separate molecule (e.g., a cDNA or a genomic or cDNA fragment produced by PCR or restriction endonuclease digestion) independent of other sequences. It also includes a recombinant nucleic acid that is part of a hybrid gene encoding additional polypeptide sequence.

By "antisense," as used herein in reference to nucleic acids, is meant a nucleic acid sequence that is complementary to the coding strand of a gene, preferably, an NRAGE gene. Preferably the antisense nucleic acid molecule decreases the amount of transcription from the gene; more preferably, the decrease is at least 10%, and most preferably, the decrease is at least 50% when administered at the maximally effective dose.

By "substantially pure antibody" is meant antibody which is at least 60%, by weight, free from proteins and naturally occurring organic molecules with which it is naturally associated. Preferably, the preparation is at least 75%, more preferably 90%, and most preferably at least 99%, by weight, antibody. A purified antibody may be obtained, for example, by affinity chromatography using recombinantly-produced protein or conserved motif peptides and standard techniques.

By "specifically binds" is meant an antibody that recognizes and binds to, for example, a human, mouse, or rat NRAGE polypeptide but does not substantially recognize and bind to other non-NRAGE molecules in a sample, e.g., a biological sample, that naturally includes protein. A preferred antibody binds to an NRAGE polypeptide sequence of FIG. 1A or FIG. 1B.

By "neutralizing antibodies" is meant antibodies that interfere with any of the biological activities of an NRAGE polypeptide, for example, the ability of NRAGE to bind to p75NTR. The neutralizing antibody may reduce the ability of an NRAGE to bind to p75NTR by 50%, more preferably by 70%, and most preferably by 90% or more. Any standard assay for the biological activity of NRAGE, including those described herein, may be used to assess potentially neutralizing antibodies that are specific for NRAGE.

By "expose" is meant to allow contact between an animal, cell, lysate or extract derived from a cell, or molecule derived from a cell, and a candidate compound.

By "treat" is meant to submit or subject an animal (e.g. a human), cell, lysate or extract derived from a cell, or molecule derived from a cell to a candidate compound.

By "candidate compound" is meant a chemical, be it naturally-occurring or artificially-derived, that is assayed for its ability to modulate an alteration in reporter gene activity or protein levels, by employing one of the assay methods described herein. Test compounds may include, for example, peptides, polypeptides, synthesized organic molecules, naturally occurring organic molecules, nucleic acid molecules, and components thereof.

By "assaying" is meant analyzing the effect of a treatment, be it chemical or physical, administered to whole animals or cells derived therefrom. The material being analyzed may be an animal, a cell, a lysate or extract derived from a cell, or a molecule derived from a cell. The analysis may be, for example, for the purpose of detecting altered gene expression, altered RNA stability, altered protein stability, altered protein levels, or altered protein biological activity. The means for analyzing may include, for example, antibody labeling, immunoprecipitation, phosphorylation assays, and methods known to those skilled in the art for detecting nucleic acids.

By "modulating" is meant changing, either by decrease or increase, in biological activity.

By "a decrease" is meant a lowering in the level of biological activity, as measured by a lowering/increasing of: a) protein, as measured by ELISA; b) reporter gene activity, as measured by reporter gene assay, for example, lacZ/β-galactosidase, green fluorescent protein, luciferase, etc.; c) mRNA, as measured by PCR relative to an internal control, for example, a "housekeeping" gene product such as β-actin or glyceraldehyde 3-phosphate dehydrogenase (GAPDH). In all cases, the lowering is preferably by 30%, more preferably by 40%, and even more preferably by 70%.

By "an increase" is meant a rise in the level of biological activity, as measured by a lowering/increasing of: a) protein, measured by ELISA; b) reporter gene activity, as measured by reporter gene assay, for example, lacZ/β-galactosidase, green fluorescent protein, luciferase, etc.; c) mRNA, as measured by PCR relative to an internal control, for example, a "housekeeping" gene product such as β-actin or glyceraldehyde 3-phosphate dehydrogenase (GAPDH). Preferably, the increase is by 5% or more, more preferably by 15% or more, even more preferably by 2-fold, and most preferably by at least 3-fold.

By "promoter" is meant a minimal sequence sufficient to direct transcription. Also included in the invention are those promoter elements which are sufficient to render promoter-dependent gene expression controllable for cell type-specific, tissue-specific, temporal-specific, or inducible by external signals or agents; such elements may be located in the 5' or 3' or intron sequence regions of the native gene.

By "operably linked" is meant that a gene and one or more regulatory sequences are connected in such a way as to permit gene expression when the appropriate molecules (e.g., transcriptional activator proteins) are bound to the regulatory sequences.

By "pharmaceutically acceptable carrier" is meant a carrier that is physiologically acceptable to the treated mammal while retaining the therapeutic properties of the compound with which it is administered. One exemplary pharmaceutically acceptable carrier is physiological saline solution. Other physiologically acceptable carriers and their formulations are known to one skilled in the art and described, for example, in *Remington: The Science and Practice of Pharmacy*, (19$^{th}$ edition), ed. A. Gennaro, 1995, Mack Publishing Company, Easton, Pa.

BRIEF DESCRIPTION OF DRAWINGS

FIG. 1A shows the polypeptide sequence for human NRAGE (SEQ ID NO: 1).

FIG. 1B shows the polypeptide sequence for rat NRAGE (SEQ ID NO: 2).

FIG. 1C shows the cDNA sequence for human NRAGE (SEQ ID NO: 3).

FIG. 1D shows the cDNA sequence for rat NRAGE (SEQ ID NO: 4).

Figure 2:
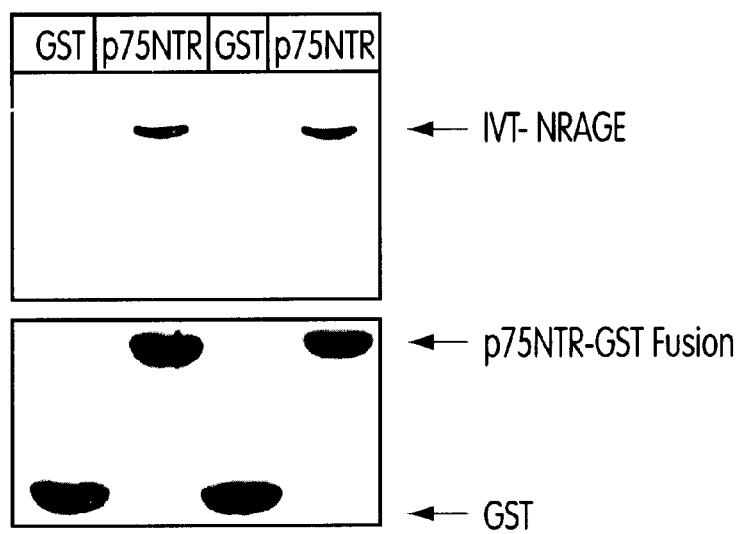
FIG. 2 is a photograph showing that NRAGE binds to p75NTR in vitro. GST or p75NTR-GST fusion proteins bound to glutathione beads were incubated with NRAGE produced by in vitro translation. Top panel shows NRAGE specifically associating with p75NTR-GST but not with GST. Bottom panel shows that equivalent amounts of GST protein were used.

Other features and advantages of the invention will be apparent from the following description of the preferred embodiments thereof and from the claims.

DETAILED DESCRIPTION OF THE INVENTION

We have discovered a signal transduction intermediate (termed "NRAGE") involved in neurotrophin signaling. We have found that NRAGE binds to p75NTR. These discoveries provide new methods for regulating cell survival, and allow for generation or discovery of drugs useful in the treatment of human diseases.

Identification of Molecules that Modulate NRAGE Biological Activity

The effect of candidate molecules on NRAGE-mediated regulation of cell survival may be measured at the level of translation by using the general approach described above with standard protein detection techniques, such as Western blotting or immunoprecipitation with an NRAGE-specific antibody (for example, the NRAGE antibody described herein).

Compounds that modulate the level of NRAGE may be purified, or substantially purified, or may be one component of a mixture of compounds such as an extract or supernatant obtained from cells (Ausubel et al., supra). In an assay of a mixture of compounds, NRAGE expression is measured in cells administered progressively smaller subsets of the compound pool (e.g., produced by standard purification techniques such as HPLC or FPLC) until a single compound or minimal number of effective compounds is demonstrated to NRAGE expression.

Compounds may also be screened for their ability to modulate NRAGE apoptosis-modulating activity or binding to p75NTR. In this approach, the degree of NRAGE apoptosis-modulating activity or binding to p75NTR in the presence of a candidate compound is compared to the degree of apoptosis-modulating activity or binding to in its absence, under equivalent conditions. Again, the screen may begin with a pool of candidate compounds, from which one or more useful modulator compounds are isolated in a stepwise fashion. Apoptosis-modulating activity and binding to may be each measured by any standard assay, for example, those described herein.

Another method for detecting compounds that modulate the activity of NRAGE is to screen for compounds that interact physically with NRAGE. These compounds may be detected by adapting interaction trap expression systems known in the art. These systems detect protein interactions using a transcriptional activation assay and are generally described by Gyuris et al. (Cell 75:791–803, 1993) and Field et al., (Nature 340:245–246, 1989), and are commercially available from Clontech (Palo Alto, Calif.). Alternatively, NRAGE or biologically active fragments thereof can be labeled with $^{125}$I Bolton-Hunter reagent (Bolton et al. Biochem. J. 133: 529, 1973). Candidate molecules previously arrayed in the wells of a multi-well plate are incubated with the labeled NRAGE, washed and any wells with labeled NRAGE complex are assayed. Data obtained using different concentrations of NRAGE are used to calculate values for the number, affinity, and association of NRAGE with the candidate molecules.

Compounds or molecules that function as modulators of NRAGE apoptosis-modulating activity may include peptide and non-peptide molecules such as those present in cell extracts, mammalian serum, or growth medium in which mammalian cells have been cultured.

A molecule that modulates NRAGE expression or NRAGE-mediated modulation of p75NTR biological activity such that there is an increase in apoptosis is considered useful in the invention; such a molecule may be used, for example, as a therapeutic to induce cell death in cells undergoing abnormal or inappropriate cell proliferation.

Similarly, a molecule that modulates NRAGE expression or NRAGE-mediated modulation of p75NTR biological activity such that there is a decrease in apoptosis is also considered useful in the invention; such a molecule may be used, for example, as a therapeutic to prevent in appropriate or abnormal cell death, such as that observed in having AIDS, cirrhosis of the liver, a neurodegenerative disease (Alzheimer's disease, Parkinson's disease, amyolateral sclerosis, and the like), a myelodysplastic syndrome, or an ischemic injury.

Therapy

To add NRAGE protein to cells in order to modulate cell apoptosis, it is necessary to obtain sufficient amounts of pure NRAGE protein from cultured cell systems that can express the protein. Delivery of the protein to the affected tissue can then be accomplished using appropriate packaging or administrating systems. Alternatively, small molecule analogs may be used and administered to act as NRAGE agonists or antagonists and in this manner produce a desired physiological effect. Methods for finding such molecules are provided herein.

Gene therapy is another potential therapeutic approach in which normal copies of the NRAGE gene or nucleic acid encoding NRAGE sense RNA are introduced into cells to successfully produce NRAGE protein, or NRAGE antisense RNA is introduced into cells that express excessive normal or mutant NRAGE. The gene must be delivered to those cells in a form in which it can be taken up and encode for sufficient protein to provide effective function.

Retroviral vectors, adenoviral vectors, adenovirus-associated viral vectors, or other viral vectors with the appropriate tropism for cells involved in a cell proliferation disease may be used as a gene transfer delivery system for a therapeutic NRAGE gene construct. Numerous vectors useful for this purpose are generally known (Miller, Human Gene Therapy 15-14, 1990; Friedman, Science 244:1275–1281, 1989; Eglitis and Anderson, BioTechniques 6:608–614, 1988; Tolstoshev and Anderson, Curr. Opin. Biotech. 1:55–61, 1990; Sharp, The Lancet 337: 1277–1278, 1991; Cornetta et al., Nucl. Acid Res. and Mol. Biol. 36: 311–322, 1987; Anderson, Science 226: 401–409, 1984; Moen, Blood Cells 17: 407–416, 1991; Miller et al., Biotech. 7: 980–990, 1989;, Le Gal La Salle et al., Science 259: 988–990, 1993; and Johnson, Chest 107: 77S–83S, 1995). Retroviral vectors are particularly well developed and have been used in clinical settings (Rosenberg et al., N. Engl. J. Med. 323: 370, 1990, Anderson et al., U.S. Pat. No. 5,399, 346). Non-viral approaches may also be employed for the introduction of therapeutic DNA into cells otherwise predicted to undergo excessive or abnormal proliferation. For example,. NRAGE may be introduced into a cell by lipofection (Felgner et al., Proc. Natl. Acad. Sci. USA 84: 7413, 1987; Ono et al., Neurosci. Lett. 117: 259, 1990; Brigham et al., Am. J. Med. Sci. 298:278, 1989; Staubinger et al., Meth. Enzymol. 101:512, 1983), asialorosonucoid-polylysine conjugation (Wu et al., J. Biol. Chem. 263:14621, 1988; Wu et al., J. Biol. Chem. 264:16985, 1989); or, less preferably, micro-injection under surgical conditions (Wolff et al., Science 247:1465, 1990).

Gene transfer could also be achieved using non-viral means requiring infection in vitro. This would include calcium phosphate, DEAE dextran, electroporation, and protoplast fusion. Liposomes may also be potentially beneficial for delivery of DNA into a cell. Although these methods are available, many of these are of lower efficiency.

Many methods for introducing vectors into cells or tissues are available and equally suitable for use in vivo, in vitro and ex vivo. For ex vivo therapy, vectors may be introduced into stem cells taken from the patient and clonally propagated for autologous transplant back into that same patient. Delivery by transfection and by liposome injections may be achieved using methods which are well known in the art. Transplantation of normal genes into the affected cells of a patient can also be useful therapy. In this procedure, a normal NRAGE gene is transferred into a cultivatable cell type, either exogenously or endogenously to the patient. These cells are then injected into the targeted tissue(s).

In the constructs described, NRAGE cDNA expression can be directed from any suitable promoter (e.g., the human cytomegalovirus (CMV), simian virus 40 (SV40), or metallothionein promoters), and regulated by any appropriate mammalian regulatory element. For example, if desired, enhancers known to preferentially direct gene expression in tumor cells may be used to direct NRAGE expression. The enhancers used could include, without limitation, those that are characterized as tissue- or cell-specific in their expression. Alternatively, if an NRAGE genomic clone is used as a therapeutic construct (for example, following isolation by hybridization with the NRAGE cDNA described above), regulation may be mediated by the cognate regulatory sequences or, if desired, by regulatory sequences derived from a heterologous source, including any of the promoters or regulatory elements described above.

Antisense based strategies may be employed to explore NRAGE gene function and as a basis for therapeutic drug design. The principle is based on the hypothesis that sequence-specific suppression of gene expression can be achieved by intracellular hybridization between mRNA and a complementary antisense species. The formation of a hybrid RNA duplex may then interfere with the processing/transport/translation and/or stability of the target NRAGE mRNA. Antisense strategies may use a variety of approaches including the use of antisense oligonucleotides and injection of antisense RNA. Antisense effects can be induced by control (sense) sequences, however, the extent of phenotypic changes are highly variable. Phenotypic effects induced by antisense effects are based on changes in criteria such as protein levels, protein activity measurement, and target mRNA levels. Such technology is now well known in the art, and sense or antisense oligomers or larger fragments, can be designed from various locations along the coding or control regions of sequences encoding NRAGE. In one example, the complementary oligonucleotide is designed from the most unique 5' sequence and used either to inhibit transcription by preventing promoter binding to the upstream nontranslated sequence or translation of an NRAGE-encoding transcript by preventing the ribosome from binding. Using an appropriate portion of the signal and 5' sequence of NRAGE, an effective antisense oligonucleotide includes any 15–20 nucleotides spanning the region which translates into the signal or 5' coding sequence of the polypeptide as shown in FIGS. 1A and 1B.

For example, NRAGE gene therapy may also be accomplished by direct administration of antisense NRAGE mRNA to a cell that is expected to undergo undesired apoptosis. The antisense NRAGE mRNA may be produced and isolated by any standard technique, but is most readily produced by in vitro transcription using an antisense NRAGE cDNA under the control of a high efficiency promoter (e.g., the T7 promoter). Administration of antisense NRAGE mRNA to cells can be carried out by any of the methods for direct nucleic acid administration described above.

Ribozymes, enzymatic RNA molecules, may also be used to catalyze the specific cleavage of RNA. The mechanism of ribozyme action involves sequence-specific hybridization of the ribozyme molecule to complementary target RNA, followed by endonucleolytic cleavage. Examples which may be used include engineered hammerhead motif ribozyme molecules that can specifically and efficiently catalyze endonucleolytic cleavage of sequences encoding NRAGE.

Specific ribozyme cleavage sites within any potential RNA target are initially identified by scanning the target molecule for ribozyme cleavage sites which include the following sequences: GUA, GUU, and GUC. Once identified, short RNA sequences of between 15 and 20 ribonucleotides corresponding to the region of the target gene containing the cleavage site may be evaluated for secondary structural features which may render the oligonucleotide inoperable. The suitability of candidate targets may also be evaluated by testing accessibility to hybridization with complementary oligonucleotides using ribonuclease protection assays.

Antisense molecules and ribozymes of the invention may be prepared by any method known in the art for the synthesis of nucleic acid molecules. These include techniques for chemically synthesizing oligonucleotides such as solid phase phosphoramidite chemical synthesis. Alternatively, RNA molecules may be generated by in vitro and in vivo transcription of DNA sequences encoding NRAGE. Such DNA sequences may be incorporated into a wide variety of vectors with suitable RNA polymerase promoters such as T7 or SP6. Alternatively, these cDNA constructs that synthesize antisense RNA constitutively or inducibly can be introduced into cell lines, cells, or tissues.

RNA molecules may be modified to increase intracellular stability and half-life. Possible modifications include, but are not limited to, the addition of flanking sequences at the 5' and/or 3' ends of the molecule or the use of phosphorothioate or 2' O-methyl rather than phosphodiesterase linkages within the backbone of the molecule. This concept can be extended in all of these molecules by the inclusion of nontraditional bases such as inosine, queosine, and wybutosine, as well as acetyl-, methyl-, thio-, and similarly modified forms of adenine, cytidine, guanine, thymine, and uridine which are not as easily recognized by endogenous endonucleases.

An alternative strategy for inhibiting NRAGE function using gene therapy involves intracellular expression of an anti-NRAGE antibody or a portion of an anti-NRAGE antibody For example, the gene (or gene fragment) encoding a monoclonal antibody that specifically binds to NRAGE and inhibits its biological activity may be placed under the transcriptional control of a cell type-specific gene regulatory sequence.

Another therapeutic approach within the invention involves administration of a recombinant NRAGE polypeptide (e.g, the ones described herein), either directly to the site of a potential or actual cell apoptotic event (for example, by injection) or systemically (for example, by any conventional recombinant protein administration technique). The dosage of NRAGE depends on a number of factors, including the size and health of the individual patient, but, generally, between 0.1 mg and 100 mg inclusive are administered per day to an adult in any pharmaceutically acceptable formulation.

In other embodiments, any of the therapeutic proteins, antagonists, antibodies, agonists, antisense sequences or vectors described above may be administered in combination with other appropriate therapeutic agents. Selection of the appropriate agents for use in combination therapy may be made by one of ordinary skill in the art, according to conventional pharmaceutical principles. The combination of therapeutic agents may act synergistically to effect the treatment or prevention of the various disorders described above. Using this approach, one may be able to achieve therapeutic efficacy with lower dosages of each agent, thus reducing the potential for adverse side effects.

An additional embodiment of the invention relates to the administration of a pharmaceutical composition, in conjunction with a pharmaceutically acceptable carrier, for any of the therapeutic effects discussed above. Such pharmaceutical compositions may consist of NRAGE, antibodies to NRAGE, mimetics, agonists, antagonists, or inhibitors of NRAGE. The compositions may be administered alone or in combination with at least one other agent, such as stabilizing compound, which may be administered in any sterile, biocompatible pharmaceutical carrier, including, but not limited to, saline, buffered saline, dextrose, and water. The compositions may be administered to a patient alone, or in combination with other agents, drugs or hormones.

Methods well known in the art for making formulations are found, for example, in *Remington: The Science and Practice of Pharmacy*, supra. Formulations for parenteral administration may, for example, contain excipients, sterile water, or saline, polyalkylene glycols such as polyethylene glycol, oils of vegetable origin, or hydrogenated napthalenes. Biocompatible, biodegradable lactide polymer, lactide/glycolide copolymer, or polyoxyethylene-polyoxypropylene copolymers may be used to control the release of the compounds. Other potentially useful parenteral delivery systems for NRAGE modulatory compounds include ethylene-vinyl acetate copolymer particles, osmotic pumps, implantable infusion systems, and liposomes. Formulations for inhalation may contain excipients, for example, lactose, or may be aqueous solutions containing, for example, polyoxyethylene-9-lauryl ether, glycocholate and deoxycholate, or may be oily solutions for administration in the form of nasal drops, or as a gel.

Diagnostics

Antibodies which specifically bind NRAGE may be used for the diagnosis of conditions or diseases characterized by expression of NRAGE, or in assays to monitor patients being treated with NRAGE, agonists, antagonists or inhibitors. The antibodies useful for diagnostic purposes may be prepared in the same manner as those described above for therapeutics. Diagnostic assays for NRAGE include methods which utilize the antibody and a label to detect NRAGE in human body fluids or extracts of cells or tissues. The antibodies may be used with or without modification, and may be labeled by joining them, either covalently or non-covalently, with a reporter molecule. A wide variety of reporter molecules which are known in the art may be used, several of which are described herein.

A variety of protocols including ELISA, RIA, and FACS for measuring NRAGE are known in the art and provide a basis for diagnosing altered or abnormal levels of NRAGE expression. Normal or standard values for NRAGE expression are established by combining body fluids or cell extracts taken from normal mammalian subjects, preferably human, with antibody to NRAGE under conditions suitable for complex formation. The amount of standard complex formation may be quantified by various methods, but preferably by photometric, means. Quantities of NRAGE expressed in subject, control and disease, samples from biopsied tissues are compared with the standard values. Deviation between standard and subject values establishes the parameters for diagnosing disease.

The nucleic acid sequences encoding NRAGE may also be used for diagnostic purposes. The nucleic acid sequences which may be used include antisense RNA and DNA molecules, and oligonucleotide sequences. The nucleic acid sequences may be used to detect and quantitate gene expression in biopsied tissues in which expression of NRAGE may be correlated with disease. The diagnostic assay may be used to distinguish between absence, presence, and excess expression of NRAGE, and to monitor regulation of NRAGE levels during therapeutic intervention.

Nucleic acid sequences encoding NRAGE may be used for the diagnosis of conditions or diseases which are associated with expression of NRAGE. The nucleic acid sequences encoding NRAGE may be used in Southern or northern analysis, dot blot, or other membrane-based technologies; in PCR technologies; or in dip stick, pIN, ELISA or chip assays utilizing fluids or tissues from patient biopsies to detect altered NRAGE expression. Such qualitative or quantitative methods are well known in the art.

The nucleotide sequences encoding NRAGE may be labeled by standard methods, and added to a fluid or tissue sample from a patient under conditions suitable for the formation of hybridization complexes. After a suitable incubation period, the sample is washed and the signal is quantitated and compared with a standard value. If the amount of signal in the biopsied or extracted sample is significantly altered from that of a comparable control sample, the nucleotide sequences have hybridized with nucleotide sequences in the sample, and the presence of altered levels of nucleotide sequences encoding NRAGE in the sample indicates the presence of the associated disease. Such assays may also be used to evaluate the efficacy of a particular therapeutic treatment regimen in animal studies, in clinical trials, or in monitoring the treatment of an individual patient.

In order to provide a basis for the diagnosis of disease associated with expression of NRAGE, a normal or standard profile for expression is established. This may be accomplished by combining body fluids or cell extracts taken from normal subjects, either animal or human, with a sequence, or a fragment thereof, which encodes NRAGE, under conditions suitable for hybridization or amplification. Standard hybridization may be quantified by comparing the values obtained from normal subjects with those from an experiment where a known amount of a substantially purified polynucleotide is used. Standard values obtained from normal samples may be compared with values obtained from samples from patients who are symptomatic for disease. Deviation between standard and subject values is used to establish the presence of disease.

Once disease is established and a treatment protocol is initiated, hybridization assays may be repeated on a regular basis to evaluate whether the level of expression in the patient begins to approximate that which is observed in the normal patient. The results obtained from successive assays may be used to show the efficacy of treatment over a period ranging from several days to months.

The following examples are to illustrate the invention. They are not meant to limit the invention in any way.

EXAMPLE 1

Isolation of a p75NTR-Interacting Protein

We performed yeast two-hybrid screens to identify molecules that directly interact with the p75NTR intracellular domain. From this, an interacting protein was identified.

The initial cDNA identified in the two-hybrid screen was used to screen a rat MAH cell cDNA library, leading to the identification of three overlapping cDNAs. The longest clone, 2.6 kilobases in length, detects a single mRNA species of 2.7 kb on Northern blots and contains a single open reading of 775 amino acids.

Similarity searches revealed that the identified protein was a member of a group of proteins termed the MAGE family (for melanoma associated antigen) whose functions remain largely unknown. The identified protein was named NRAGE. Like the MAGE family members, NRAGE contains a highly conserved 200 amino acid MAGE Homology Domain (MHD). Many genes of the MAGE family consist of little more than this conserved domain but some, including NRAGE, are much larger proteins. In addition to similarity to the MAGE family, NRAGE contains an extended stretch of proline-rich tandem repeats that show a low degree of similarity to helical heptad repeats present in neurofilaments.

In addition to the rat sequence, we have cloned human NRAGE cDNA. NRAGE is highly conserved between human and rat, with over 90% of amino acid residues conserved.

EXAMPLE 2

Production of Antibodies to NRAGE

Anti-NRAGE antibodies were produced by injecting rabbits with peptides representing NRAGE sequences that were chemically conjugated to keyhole lympet hemocyanin. Antibody 1 represents amino acid sequence 702–716 of NRAGE, while antibody 2 represents amino acid sequence 718–732. Rabbits were injected with the same peptides two weeks later to improve the titer. Sera were collected three, five, and seven weeks after the injection.

EXAMPLE 3

NRAGE Interacts with p75NTR

Figure 3:
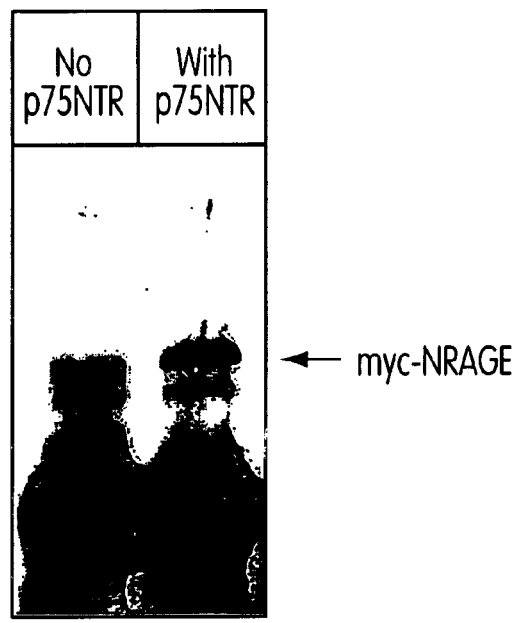
FIG. 3 is a photograph showing that overexpressed NRAGE and p75NTR interact in vitro. 293T cells were transfected with myc-NRAGE in the presence and absence of p75NTR. Cells were lysed and immunoprecipitated with a p75NTR monoclonal antibody.

As described herein, NRAGE was identified by virtue of its interaction with the p75NTR intracellular domain. We first demonstrated this interaction in yeast, using the two-hybrid system. We also demonstrated this interaction in vitro; in vitro translated NRAGE binds to GST-p75NTR, but not to GST alone (FIG. 2). Additionally, co-immunoprecipitations show that NRAGE and p75NTR interact when both are overexpressed in 293 cells (FIG. 3), and that endogenous NRAGE and p75NTR interact in PC12 cells in the absence of neurotrophin.

In many signaling events, receptor activation causes aggregation of intracellular domains and subsequent localization of cytosolic signaling particles to the plasmalemma. For example, ligand-mediated aggregation of TNF receptor superfamily members results in binding of cytosolic TRAF and TRADD protein that, in turn, aggregate and activate downstream kinases. Alternatively, some receptors associate constitutively with cytosolic molecules which are released following receptor activation. In one example, the "silencer of death domain" (SODD) protein is constitutively bound to the TNF-R1 and DR3 receptors and is released upon receptor activation. Our data are consistent with the hypothesis that p75NTR binds NRAGE constitutively and that NRAGE is released from the receptor following activation. It is likely that NRAGE is released from p75NTR as a function of neurotrophin binding, resulting in a rise of cystolic NRAGE levels.

The proliferative phase of neuronal loss occurs early in development. In this phase, neuroblasts leave the cell cycle and either become viable post-mitotic neurons or die. Neuronal cell death is widespread during this phase. The connection between p75NTR and NRAGE, described herein, raises the possibility that a p75NTR-NRAGE pathway regulates apoptotic events during this first phase of neuronal loss. Other work directly supports a role for p75NTR in apoptotic events. Apoptosis within the developing spinal cord at E10.5, at the peak phase of neurogenesis, occurs both within the ependymal zone, which consists mostly of neuronal precursors, and within the mantle zone, which contains newly born neurons. In p75NTR –/– mice, the incidence of apoptosis in the spinal cord at this time is sharply reduced, particularly in the mantle zone. It is not known if these cells maintained in the spinal cord of p75NTR –/– remain viable, but increased numbers of basal forebrain cholinergic and sympathetic neurons have been noted in the p75NTR –/– mouse, and it is possible that these supernumerary neurons arise due to a defect in apoptosis. Other data consistent with a role for p75NTR in neuronal loss has emerged from detailed analysis of NT3 –/– mice. The majority of wild-type DRG neuroblasts exit the cell cycle at E11/E12 to form postmitotic neurons, while NT-3 –/– neuroblasts precede through the normal G1 restriction point and die by apoptosis in S phase. This early phase of cell death is not observed in trkC –/– mice. As a result, the NT3 –/– mice have about 50% fewer DRG neurons at P0 than do trkC –/– mice. These data suggest that NT-3 normally acts to suppress apoptosis in the developing. DRG by acting through a receptor other than trkC.

p75NTR is expressed in essentially all of the sensory precursors at this stage of DRG development and it is likely that p75NTR, which is abundantly expressed in the DRG neurons at this stage, reduces apoptosis in the developing DRG. Another possibility is that NT-3 acts through trkA to mediate these effects. This is unlikely since NT-3 does not support survival through trkA in the developing DRG (White, 1996) and since NT-3 is a poor ligand for trkA, particularly when trkA is co-expressed with p75NTR. Together, these recent studies raise the possibility that p75NTR may help regulate apoptotic events.

EXAMPLE 4

The Effect of Neurotrophin Binding p75NTR on NRAGE Translocation

The analysis of the interaction of p75NTR with downstream signaling molecules and its regulation is complicated by the fact that there are at least four neurotrophins capable of binding p75NTR and exerting differential effects. Furthermore, p75NTR is often co-expressed with members of the trk family and there is extensive crosstalk between p75NTR and trk receptors, with p75NTR regulating trk activity in some circumstances and trk regulating p75NTR in others.

p75NTR regulates the cellular location of NRAGE. In cells lacking p75NTR, NRAGE is predominantly located in the cytosol. When co-expressed with p75NTR, however, NRAGE is located mainly at the plasma membrane. Addition of neurotrophin to cultures of p75NTR-expressing cells causes a reduction in the plasma membrane-associated NRAGE, and an increase in cytosolic NRAGE. When p75NTR and trkA are co-expressed, they form a stable complex. NRAGE fragments disrupt this complex. This suggests that when p75NTR and trkA are coexpressed, they form a complex that requires NRAGE.

To unravel these complex interactions, a comprehensive analysis of the effect of the various neurotrophins on the association of NRAGE with p75NTR in PC12nnr cells, which express both p75NTR and NRAGE but lack trk expression, can be performed. Immunoprecipitates of p75NTR before and after stimulation with one of the four neurotrophins for period up to two hours and at concentrations up to 250 ng/ml are analyzed for the presence of NRAGE. In parallel experiments, immunoprecipitates of NRAGE following the same treatment conditions are analyzed for the presence of p75NTR. It is very likely that the NRAGE-p75NTR complex is differentially affected by the various neurotrophins. To determine how the trk receptor contributes to NRAGE mobilization, similar experiments are performed using this cell system before and after infection with recombinant adenovirus encoding either wild-type trkA, kinase-dead trkA or lacZ (used as a negative control), followed by analysis of NRAGE translocation. Preferably, untreated and neurotrophin-treated PC12nnr5 cells are processed by differential centrifugation to separate membrane, nuclear, and cytosolic compartments. Each or these are analyzed for NRAGE content by immunoblot. Finally, an immunocytochemical approach is used to evaluate localization of NRAGE in intact cells. Myc- and GFP-tagged forms of NRAGE show identical distributions when expressed in COS7 and 293A cells, indicating that tagging does not affect NRAGE distribution. We can examine the distribution of tagged $NRAGE^{wt}$ in the presence and absence of p75NTR and in the presence and absence of neurotrophin, using standard immunocytochemical techniques. We can also examine the subcellular distribution of untagged NRAGE using affinity purified anti-NRAGE antibodies.

Other Embodiments

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the invention.

---

What is claimed is:

1. A method for identifying a compound that modulates apoptosis, said method comprising:

(a) contacting (i) a p75NTR polypeptide; (ii) an NRAGE polypeptide comprising at least 90% sequence identity to SEQ ID NO: 1 or SEQ ID NO: 2, said NRAGE polypeptide capable of binding said p75NTR polypeptide; and (iii) a candidate compound; and (b) monitoring the level of binding of said NRAGE polypeptide to said p75NTR polypeptide, wherein a change in said level of binding in the presence of said candidate compound, relative to a level of binding of said NRAGE polypeptide to said p75NTR polypeptide in the absence of said candidate compound, identifies said candidate compound as a compound that modulates apoptosis.

2. The method of claim 1, wherein said contacting takes place in a cell.

3. The method of claim 1, wherein said cell is in a mammal.

4. The method of claim 1, wherein said cell is from a mammal.

5. The method of claim 4, wherein said mammal is a human or a rodent.

6. The method of claim 1, wherein said contacting takes place in a cell-free system.

7. The method of claim 1, wherein said NRAGE polypeptide is human NRAGE (SEQ ID NO: 1) or rat NRAGE (SEQ ID NO: 2).

8. The method of claim 6, wherein said NRAGE polypeptide is human NRAGE (SEQ ID NO: 1) or rat NRAGE (SEQ ID NO: 2).

9. The method of claim 2, wherein said cell is in vitro.

10. The method of claim 9, wherein said NRAGE polypeptide is human NRAGE (SEQ ID NO: 1) or rat NRAGE (SEQ ID NO: 2).

* * * * *

SEQUENCE LISTING

<160> NUMBER OF SEQ ID NOS: 4

<210> SEQ ID NO 1
<211> LENGTH: 778
<212> TYPE: PRT
<213> ORGANISM: Homo sapiens

<400> SEQUENCE: 1

```
Met Ala Gln Lys Met Asp Cys Gly Ala Gly Leu Leu Gly Phe Gln Ala
1               5                   10                  15
Glu Ala Ser Val Glu Asp Ser Ala Leu Leu Met Gln Thr Leu Met Glu
            20                  25                  30
Ala Ile Gln Ile Ser Glu Ala Pro Pro Thr Asn Gln Ala Thr Ala Ala
        35                  40                  45
Ala Ser Pro Gln Ser Ser Gln Pro Pro Thr Ala Asn Glu Met Ala Asp
    50                  55                  60
Ile Gln Val Ser Ala Ala Ala Arg Pro Lys Ser Ala Phe Lys Val
65                  70                  75                  80
Gln Asn Ala Thr Thr Lys Gly Pro Asn Gly Val Tyr Asp Phe Ser Gln
                85                  90                  95
Ala His Asn Ala Lys Asp Val Pro Asn Thr Gln Pro Lys Ala Ala Phe
            100                 105                 110
Lys Ser Gln Asn Ala Thr Ser Lys Gly Pro Asn Ala Ala Tyr Asp Phe
        115                 120                 125
Ser Gln Ala Ala Thr Thr Gly Glu Leu Ala Ala Asn Lys Ser Glu Met
    130                 135                 140
Ala Phe Lys Ala Gln Asn Ala Thr Thr Lys Val Gly Pro Asn Ala Thr
145                 150                 155                 160
Tyr Asn Phe Ser Gln Ser Leu Asn Ala Asn Asp Leu Ala Asn Ser Arg
```

-continued

```
                165                 170                 175
Pro Lys Thr Pro Phe Lys Ala Trp Asn Asp Thr Thr Lys Ala Pro Thr
            180                 185                 190
Ala Asp Thr Gln Thr Gln Asn Val Asn Gln Ala Lys Met Ala Thr Ser
        195                 200                 205
Gln Ala Asp Ile Glu Thr Asp Pro Gly Ile Ser Glu Pro Asp Gly Ala
    210                 215                 220
Thr Ala Gln Thr Ser Ala Asp Gly Ser Gln Ala Gln Asn Leu Glu Ser
225                 230                 235                 240
Arg Thr Ile Ile Arg Gly Lys Arg Thr Arg Lys Ile Asn Asn Leu Asn
                245                 250                 255
Val Glu Glu Asn Ser Ser Gly Asp Gln Arg Arg Ala Pro Leu Ala Ala
            260                 265                 270
Gly Thr Trp Arg Ser Ala Pro Val Pro Val Thr Thr Gln Asn Pro Pro
        275                 280                 285
Gly Ala Pro Pro Asn Val Leu Trp Gln Thr Pro Leu Ala Trp Gln Asn
    290                 295                 300
Pro Ser Gly Trp Gln Asn Gln Thr Ala Arg Gln Thr Pro Pro Ala Arg
305                 310                 315                 320
Gln Ser Pro Pro Ala Arg Gln Thr Pro Pro Ala Trp Gln Asn Pro Val
                325                 330                 335
Ala Trp Gln Asn Pro Val Ile Trp Pro Asn Pro Val Ile Trp Gln Asn
            340                 345                 350
Pro Val Ile Trp Pro Asn Pro Ile Val Trp Pro Gly Pro Val Val Trp
        355                 360                 365
Pro Asn Pro Leu Ala Trp Gln Asn Pro Gly Trp Gln Thr Pro Pro
    370                 375                 380
Gly Trp Gln Thr Pro Pro Gly Trp Gln Gly Pro Pro Asp Trp Gln Gly
385                 390                 395                 400
Pro Pro Asp Trp Pro Leu Pro Pro Asp Trp Pro Leu Pro Pro Asp Trp
                405                 410                 415
Pro Leu Pro Thr Asp Trp Pro Leu Pro Pro Asp Trp Ile Pro Ala Asp
            420                 425                 430
Trp Pro Ile Pro Pro Asp Trp Gln Asn Leu Arg Pro Ser Pro Asn Leu
        435                 440                 445
Arg Pro Ser Pro Asn Ser Arg Ala Ser Gln Asn Pro Gly Ala Ala Gln
    450                 455                 460
Pro Arg Asp Val Ala Leu Leu Gln Glu Arg Ala Asn Lys Leu Val Lys
465                 470                 475                 480
Tyr Leu Met Leu Lys Asp Tyr Thr Lys Val Pro Ile Lys Arg Ser Glu
                485                 490                 495
Met Leu Arg Asp Ile Ile Arg Glu Tyr Thr Asp Val Tyr Pro Glu Ile
            500                 505                 510
Ile Glu Arg Ala Cys Phe Val Leu Glu Lys Lys Phe Gly Ile Gln Leu
        515                 520                 525
Lys Glu Ile Asp Lys Glu Glu His Leu Tyr Ile Leu Ile Ser Thr Pro
    530                 535                 540
Glu Ser Leu Ala Gly Ile Leu Gly Thr Thr Lys Asp Thr Pro Lys Leu
545                 550                 555                 560
Gly Leu Leu Leu Val Ile Leu Gly Val Ile Phe Met Asn Gly Asn Arg
                565                 570                 575
Ala Ser Glu Ala Val Leu Trp Glu Ala Leu Arg Lys Met Gly Leu Arg
            580                 585                 590
Pro Gly Val Arg His Pro Leu Leu Gly Asp Leu Arg Lys Leu Leu Thr
        595                 600                 605
Tyr Glu Phe Val Lys Gln Lys Tyr Leu Asp Tyr Arg Arg Val Pro Asn
    610                 615                 620
Ser Asn Pro Pro Glu Tyr Glu Phe Leu Trp Gly Leu Arg Ser Tyr His
625                 630                 635                 640
Glu Thr Ser Lys Met Lys Val Leu Arg Phe Ile Ala Glu Val Gln Lys
                645                 650                 655
Arg Asp Pro Arg Asp Trp Thr Ala Gln Phe Met Glu Ala Ala Asp Glu
            660                 665                 670
Ala Leu Asp Ala Leu Asp Ala Ala Glu Ala Glu Ala Arg Ala
        675                 680                 685
Glu Ala Arg Thr Arg Met Gly Ile Gly Asp Glu Ala Val Ser Gly Pro
    690                 695                 700
Trp Ser Trp Asp Asp Ile Glu Phe Glu Leu Leu Thr Trp Asp Glu Glu
705                 710                 715                 720
Gly Asp Phe Gly Asp Pro Trp Ser Arg Ile Pro Phe Thr Phe Trp Ala
                725                 730                 735
Arg Tyr His Gln Asn Ala Arg Ser Arg Phe Pro Gln Thr Phe Ala Gly
            740                 745                 750
Pro Ile Ile Gly Pro Gly Gly Thr Ala Ser Ala Asn Phe Ala Ala Asn
        755                 760                 765
Phe Gly Ala Ile Gly Phe Phe Trp Val Glu
    770                 775
```

-continued

<210> SEQ ID NO 2
<211> LENGTH: 775
<212> TYPE: PRT
<213> ORGANISM: Rattus norvegicus

<400> SEQUENCE: 2

```
Met Ala Gln Lys Pro Asp Gly Gly Ala Gly Leu Arg Gly Phe Gln Ala
 1               5                  10                  15
Glu Ala Ser Val Glu Asp Ser Ala Leu Leu Val Gln Thr Leu Met Glu
                20                  25                  30
Ala Ile Gln Ile Ser Glu Ala Pro Pro Thr Ser Gln Ala Thr Ala Ala
            35                  40                  45
Ala Ser Gly Pro Asn Ala Ser Pro Gln Ser Ser Gln Pro Pro Thr Ala
        50                  55                  60
Asn Glu Lys Ala Asp Thr Glu Val Ser Ala Ala Ala Arg Pro Lys
 65                  70                  75                  80
Thr Gly Phe Lys Ala Gln Asn Thr Thr Thr Lys Gly Pro Asn Asp Tyr
                 85                  90                  95
Ser Gln Ala Arg Asn Ala Lys Glu Met Pro Lys Asn Gln Pro Lys Val
                100                 105                 110
Ala Phe Lys Ser Gln Asn Ala Thr Ser Lys Gly Pro His Ala Ala Ser
            115                 120                 125
Asp Phe Ser His Ala Ala Ser Thr Gly Lys Ser Ala Ala Lys Lys Ser
        130                 135                 140
Glu Met Ala Phe Lys Gly Gln Asn Thr Thr Lys Ala Gly Pro Ser
145                 150                 155                 160
Ala Thr Tyr Asn Phe Thr Gln Ser Pro Ser Ala Asn Glu Met Thr Asn
                165                 170                 175
Asn Gln Pro Lys Thr Ala Lys Ala Trp Asn Asp Thr Thr Lys Ile Pro
            180                 185                 190
Gly Ala Asp Ala Gln Thr Gln Asn Val Asn Gln Ala Lys Met Ala Asp
        195                 200                 205
Val Gly Thr Ser Ala Gly Ile Ser Glu Thr Asp Gly Ala Ala Ala Gln
    210                 215                 220
Thr Ser Ala Asp Gly Ser Gln Ala Gln Asn Val Glu Ser Arg Thr Ile
225                 230                 235                 240
Ile Arg Gly Lys Arg Thr Arg Lys Ile Asn Asn Leu Asn Val Glu Glu
                245                 250                 255
Asn Ser Asn Gly Asp Gln Arg Arg Ala Ser Leu Ala Ser Gly Asn Trp
            260                 265                 270
Arg Ser Ala Pro Val Pro Val Thr Thr Gln Asn Pro Pro Gly Ala Pro
        275                 280                 285
Pro Asn Val Leu Trp Gln Thr Pro Leu Ala Trp Gln Asn Pro Ser Gly
    290                 295                 300
Trp Gln Asn Gln Thr Ala Arg Gln Thr Pro Pro Ala Arg Gln Ser Pro
305                 310                 315                 320
Pro Ala Arg Gln Thr Pro Ser Ala Trp Gln Asn Pro Val Ala Trp Gln
                325                 330                 335
Asn Pro Val Ile Trp Pro Asn Pro Val Ile Trp Gln Asn Pro Val Ile
            340                 345                 350
Trp Pro Asn Pro Ile Val Trp Pro Gly Pro Ile Val Trp Pro Asn Pro
        355                 360                 365
Met Ala Trp Gln Ser Thr Pro Gly Trp Gln Ser Pro Pro Ser Trp Gln
    370                 375                 380
Ala Pro Pro Ser Trp Gln Ser Pro Gln Asp Trp Gln Gly Pro Pro Asp
385                 390                 395                 400
Trp Gln Leu Pro Pro Asp Trp Ser Met Pro Pro Asp Trp Ser Phe Pro
                405                 410                 415
Ser Asp Trp Pro Phe Pro Pro Asp Trp Ile Pro Ala Asp Trp Pro Ile
            420                 425                 430
Pro Pro Asp Trp Gln Asn Leu Arg Pro Ser Pro Asn Leu Arg Ser Ser
        435                 440                 445
Pro Asn Ser Arg Ala Ser Gln Asn Gln Gly Pro Pro Gln Pro Arg Asp
    450                 455                 460
Val Ala Leu Leu Gln Glu Arg Ala Asn Lys Leu Val Lys Tyr Leu Met
465                 470                 475                 480
Leu Lys Asp Tyr Thr Lys Val Pro Ile Lys Arg Ser Glu Met Leu Arg
                485                 490                 495
Asp Ile Ile Arg Glu Tyr Asp Val Tyr Pro Glu Ile Ile Glu Arg
            500                 505                 510
Ala Cys Phe Val Leu Glu Lys Lys Phe Gly Ile Gln Leu Lys Glu Ile
        515                 520                 525
Asp Lys Glu Glu His Leu Tyr Ile Leu Ile Ser Thr Pro Glu Ser Leu
    530                 535                 540
Ala Gly Ile Leu Gly Thr Thr Lys Asp Thr Pro Lys Leu Gly Leu Leu
545                 550                 555                 560
Leu Val Ile Leu Gly Ile Ile Phe Met Asn Gly Asn Arg Ala Thr Glu
                565                 570                 575
```

-continued

```
Ala Val Leu Trp Glu Ala Leu Arg Lys Met Gly Leu Arg Pro Gly Val
            580                 585                 590
Arg His Pro Leu Leu Gly Asp Leu Arg Lys Leu Leu Thr Tyr Glu Phe
        595                 600                 605
Val Lys Gln Lys Tyr Leu Asp Tyr Arg Arg Val Pro Asn Ser Asn Pro
    610                 615                 620
Pro Glu Tyr Glu Phe Leu Trp Gly Leu Arg Ser Tyr His Glu Thr Ser
625                 630                 635                 640
Lys Met Lys Val Leu Arg Phe Ile Ala Glu Val Gln Lys Arg Asp Pro
                645                 650                 655
Arg Asp Trp Thr Ala Gln Phe Met Glu Ala Ala Asp Glu Ala Leu Asp
            660                 665                 670
Ala Leu Asp Ala Ala Ala Ala Glu Ala Glu Ala Arg Ala Glu Ala Arg
        675                 680                 685
Asn Arg Met Gly Ile Gly Asp Glu Ala Val Ser Gly Pro Trp Ser Trp
    690                 695                 700
Asp Asp Ile Glu Phe Glu Leu Leu Thr Trp Asp Glu Glu Gly Asp Phe
705                 710                 715                 720
Gly Asp Pro Trp Ser Arg Ile Pro Phe Thr Phe Trp Ala Arg Tyr His
                725                 730                 735
Gln Asn Ala Arg Ser Arg Phe Pro Gln Ala Phe Thr Gly Pro Ile Ile
            740                 745                 750
Gly Pro Ser Gly Thr Ala Thr Ala Asn Phe Ala Ala Asn Phe Gly Ala
        755                 760                 765
Ile Gly Phe Phe Trp Val Glu
    770                 775

<210> SEQ ID NO 3
<211> LENGTH: 2711
<212> TYPE: DNA
<213> ORGANISM: Homo sapiens

<400> SEQUENCE: 3
ggcacgagga gagtgcggct gctgagagcc gagcccagca atcccgatcc tctgagtcgt    60
gaagaaggga ggcagcgagg gggttggggt tggggcctga aagccccca ggctccgctc    120 ttgccagagg gacaggagcc atggcccaga aaatggactg tggtgcgggc ctcctcggct    180
tccaggctga ggcctccgta gaagacagcg ccttgcttat gcagaccttg atggaggcca    240
tccagatctc agaggctcca cctactaacc aggccaccgc agctgctagt ccccagagtt    300
cacagccccc aactgccaat gagatggctg acattcaggt ttcagcagct gccgctaggc    360
ctaagtcagc cttttaaagtc cagaatgcca ccacaaaagg cccaaatggt gtctatgatt    420
tctctcaggc tcataatgcc aaggatgtgc ccaacacgca gcccaaggca gcctttaagt    480
cccaaaatgc tacctccaaa ggtccaaatg ctgcctatga tttttcccag gcagcaacca    540
ctggtgagtt agctgctaac aagtctgaga tggccttcaa ggcccagaat gccactacta    600
aagtgggccc aaatgccacc tacaatttct ctcagtctct caatgccaat gacctggcca    660
acagcaggcc taagaccccct ttcaaggctt ggaatgatac cactaaggcc caacagctg    720 atacccagac ccagaatgta aatcaggcca aatggccac ttcccaggct gacatagaga    780
ccgacccagg tatctctgaa cctgacggtg caactgcaca gacatcagca gatggttccc    840
aggctcagaa tctggagtcc cggacaataa ttcggggcaa gaggacccgc aagattaata    900
acttgaatgt tgaagagaac agcagtgggg atcagaggcg ggccccactg ctgcagggaa    960
cctggaggtc tgcaccagtt ccagtgacca ctcagaaccc ccctggcgca ccccccaatg    1020
tgctctggca gacgccattg gcttggcaga ccccctcagg ctggcaaaac cagacagcca    1080
ggcagacccc accagcacgt cagagccctc cagctaggca gacccccacca gcctggcaga    1140 acccagtcgc ttggcagaac ccagtgattt ggccaaaccc agtaatctgg cagaacccag    1200
tgatctggcc aaacccccatt gtctggcccg gccctgttgt ctggccgaat ccactggcct    1260
ggcagaatcc acctggatgg cagactccac ctggatggca gaccccaccg ggctggcagg    1320
```

-continued

| | |
|---|---|
| gtcctccaga ctggcaaggt cctcctgact ggccgctacc acccgactgg ccactgccac | 1380 |
| ctgattggcc acttcccact gactggccac taccacctga ctggatcccc gctgattggc | 1440 |
| caattccacc tgactggcag aacctgcgcc cctcgcctaa cctgcgccct ctcccaact | 1500 |
| cgcgtgcctc acagaaccca ggtgctgcac agccccgaga tgtggccctt cttcaggaaa | 1560 |
| gagcaaataa gttggtcaag tacttgatgc ttaaggacta cacaaaggtg cccatcaagc | 1620 |
| gctcagaaat gctgagagat atcatccgtg aatacactga tgtttatcca gaaatcattg | 1680 |
| aacgtgcatg ctttgtccta gagaagaaat ttgggattca actgaaagaa attgacaaag | 1740 |
| aagaacacct gtatattctc atcagtaccc ccgagtccct ggctggcata ctgggaacga | 1800 |
| ccaaagacac acccaagctc ggtctcctct tggtgattct gggtgtcatc ttcatgaatg | 1860 |
| gcaaccgtgc cagtgaggct gtcctctggg aggcactacg caagatggga ctgcgtcctg | 1920 |
| gggtgagaca tcccctcctt ggagatctaa ggaaacttct cacctatgag tttgtaaagc | 1980 |
| agaaatacct ggactacaga cgagtgccca acagcaaccc cccggagtat gagttcctct | 2040 |
| ggggcctccg ttcctaccat gagactagca agatgaaagt gctgagattc attgcagagg | 2100 |
| ttcagaaaag agaccctcgt gactggactg cacagttcat ggaggctgca gatgaggcct | 2160 |
| tggatgctct ggatgctgct gcagctgagg ccgaagcccg ggctgaagca agaacccgca | 2220 |
| tgggaattgg agatgaggct gtgtctgggc cctggagctg ggatgacatt gagtttgagc | 2280 |
| tgctgacctg ggatgaggaa ggagattttg gagatccctg gtccagaatt ccatttacct | 2340 |
| tctgggccag ataccaccag aatgcccgct ccagattccc tcagacccttt gccggtccca | 2400 |
| ttattggtcc tggtggtaca gccagtgcca acttcgctgc caactttggt gccattggtt | 2460 |
| tcttctgggt tgagtgagat gttggatatt gctatcaatc gcagtagtct ttcccctgtg | 2520 |
| tgagctgaag cctcagattc cttctaaaca cagctatcta gagagccaca tcctgttgac | 2580 |
| tgaaagtggc atgcaagata aatttatttg ctgttccttg tctactgctt ttttttcccct | 2640 |
| tgtgtgctgt caagttttgg tatcagaaat aaacattgaa attgcaaagt gaaaaaaaaa | 2700 |
| aaaaaaaaa a | 2711 |

<210> SEQ ID NO 4
<211> LENGTH: 2824
<212> TYPE: DNA
<213> ORGANISM: Rattus norvegicus

<400> SEQUENCE: 4

| | |
|---|---|
| cggccgcgtc gaccgggact cttatttgga cagtgatctg ttgcgcatgc gcggggcttc | 60 |
| ctgaggcggt gggtggtata ttaggcgaag aggcggggtc gcccgagctg ccgcgctggc | 120 |
| attttctcct ggacaaggag agagtgcggg tgcagagagc ggagcagagc agtcccgatc | 180 |
| ctctgagtcg tgaagaagga agcaacgaag ggggttgggg ttgggcctg aggcaaggct | 240 |
| ctgctcttgc cagagagaca agagctatgg ctcagaaacc ggacggcggt gcaggcctcc | 300 |
| gcggcttcca ggcagaggcc tctgtagaag acagcgcctt gcttgtgcag accttgatgg | 360 |
| aagccatcca gatctccgag gctccgccca ccagccaggc cacagcagct gccagtgggc | 420 |
| cgaatgctag tccccagagt tcacagcccc caactgccaa tgagaaggct gatactgagg | 480 |
| tttcagcagc tgctgccagg cctaagacag gctttaaggc ccagaatacc accacaaagg | 540 |
| ggccaaatga ttactctcag gcacgtaatg ccaaggagat gcccaagaat cagcctaagg | 600 |
| tggcctttaa gtcacagaat gccacctcta aggtccaca tgctgcctct gatttttccc | 660 |
| atgcagcatc cacaggcaaa tcagcagcta aaaagtctga atggcctttt aagggtcaga | 720 |

-continued

```
ataccactac taaggctggc cccagtgcca cctacaattt cactcagtct cccagtgcca     780
atgagatgac caacaaccag cctaagacag ctaaggcttg gaatgacacc actaagatcc     840
ctggagctga tgcccagacc cagaatgtaa accaggccaa aatggctgac gtagggacca     900
gtgcaggtat ctctgaaact gacggtgcag cagcccagac ctcagcagat ggctcccagg     960
ctcagaatgt ggagtcccgg actataattc ggggcaagag gacccgcaag attaataact    1020
tgaatgtgga agagaacagc aatggggacc aaaggcgtgc ctcgctggct tccgggaact    1080
ggaggtctgc tccggttcca gtaaccactc agaacccacc tggcgcaccc cctaatgtgc    1140
tgtggcagac accactggct tggcagaacc catcaggctg gcaaaaccag acagccaggc    1200
agaccccacc agcacgtcag agtcccccag ctaggcagac accatcagct tggcagaacc    1260
ccgttgcatg gcagaatcca gtgatctggc ctaacccagt gatctggcag aatccagtga    1320
tctggccaaa cccattgtc tggcctggcc caattgtctg gccaaaccca atggcctggc    1380
agagtacacc tggatggcag agcccaccca gttggcaggc tccacctagt tggcagagcc    1440
ctcaagattg gcaaggccct ccagattggc agttaccacc tgactggtca atgcctcctg    1500
actggtcctt tccctctgac tggccttttc cacctgactg gatccctgcc gactggccaa    1560
ttccacccga ctggcagaac ttacgaccct cacctaatct gagatcctcc cccaactctc    1620
gtgcctcaca gaaccagggt cctccacagc cccgagatgt ggcccttctt caggaaagag    1680
caaataagct ggtcaagtac ttgatgctta aagactacac gaaggtgccc atcaagcgct    1740
cagaaatgct gagagatatc atccgagaat acactgatgt ttatccagaa atcattgaac    1800
gcgcatgctt tgtcctggag aagaaatttg gaatccagct caaggaaatc gacaaagaag    1860
agcatctgta tatcctcatc agtacccctg aatccctggc tggcatactg ggaacgacca    1920
aagacacacc gaagctaggc ctcctcttag tgattctggg cattatcttc atgaatggca    1980
accgtgccac tgaggccgtc ctctgggaag cactgcgcaa gatgggacta cgtcctgggg    2040
tcagacatcc cctccttggc gatctgagga aacttcttac ttacgagttt gtaaagcaga    2100
aatacctgga ctacagacga gtgcccaaca gcaaccctcc tgagtatgag ttcctctggg    2160
gcctccgctc ctaccatgag actagcaaga tgaaagtgct gagattcatt gcagaggttc    2220
agaagagaga ccctcgtgac tggactgcac agttcatgga agctgcagat gaagccttgg    2280
atgctctgga tgctgctgca gctgaggcag aggcccgggc cgaagcaaga aaccgcatgg    2340
ggattggaga cgaggctgtg tctgggccct ggagctggga tgacattgag tttgagctgc    2400
tgacctggga tgaggaagga gattttggag atccttggtc caggatcccc tttaccttct    2460
gggccagata ccaccagaat gcccgctcca ggtttcccca ggcctttacc ggccccatca    2520
ttggccccag cggcactgcc accgccaact tcgccgccaa cttcggtgcc attggcttct    2580
tctgggttga gtaaagtgtc agatactgct catcatttgc aatagttttc cctgagtgag    2640
gctgaagcct cagattcctt caaaacacag ctatctagag agccacatcc tgttgactga    2700
gagtggcatg caagataaat ttatttgcta ttctgtctat tactttttt tccttgtgtg    2760
ttgtcaagtt ttggtatcag aaataaatgt tgaaattgca aagtgaaaaa aaaaaaaaa    2820
aaaa                                                                  2824
```